US009186336B2

(12) United States Patent
Zeitels

(10) Patent No.: US 9,186,336 B2
(45) Date of Patent: Nov. 17, 2015

(54) METHODS OF TREATING VASCULAR LESIONS

(75) Inventor: Steven M. Zeitels, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/147,844

(22) PCT Filed: Feb. 5, 2010

(86) PCT No.: PCT/US2010/023295
§ 371 (c)(1),
(2), (4) Date: Nov. 21, 2011

(87) PCT Pub. No.: WO2010/091234
PCT Pub. Date: Aug. 12, 2010

(65) Prior Publication Data
US 2012/0065573 A1 Mar. 15, 2012

Related U.S. Application Data

(60) Provisional application No. 61/150,476, filed on Feb. 6, 2009, provisional application No. 61/151,158, filed on Feb. 9, 2009, provisional application No. 61/167,331, filed on Apr. 7, 2009.

(51) Int. Cl.
*A61K 31/00* (2006.01)
*C07K 16/22* (2006.01)

(52) U.S. Cl.
CPC ............... *A61K 31/00* (2013.01); *C07K 16/22* (2013.01); *C07K 2317/24* (2013.01); *C07K 2317/54* (2013.01); *C07K 2317/55* (2013.01)

(58) Field of Classification Search
CPC ............... C07K 16/22; C07K 2317/24; C07K 2317/54; C07K 2317/55; A61K 2039/505; A61K 2039/54; A61K 2039/541; A61K 2039/544; A61K 2039/542; A61K 31/00; A61N 5/00; A61N 5/067
See application file for complete search history.

(56) References Cited

U.S. PATENT DOCUMENTS

| | | | | |
|---|---|---|---|---|
| 5,092,314 | A * | 3/1992 | Zeitels | 600/194 |
| 5,518,999 | A * | 5/1996 | Nakamura et al. | 514/12.2 |
| 6,342,219 | B1 * | 1/2002 | Thorpe et al. | 424/145.1 |
| 2003/0055014 | A1 * | 3/2003 | Bratzler | 514/44 |
| 2005/0240147 | A1 * | 10/2005 | Makower et al. | 604/96.01 |
| 2006/0095066 | A1 * | 5/2006 | Chang et al. | 606/199 |
| 2008/0248033 | A1 * | 10/2008 | Ferrara et al. | 424/133.1 |

FOREIGN PATENT DOCUMENTS

| EP | 1619501 | 1/2006 |
|---|---|---|
| JP | 2005-511576 | 4/2005 |
| JP | 2007-505938 | 3/2007 |
| WO | 03/039404 | 5/2003 |
| WO | 2005/027972 | 3/2005 |
| WO | 2007/047646 | 4/2007 |
| WO | 2007/121154 | 10/2007 |

OTHER PUBLICATIONS

Yu et al, Investigative Ophthalmology & Visual Science 49(2): 522-527, Feb. 2008.*
Witte et al, Cancer and Metastasis Reviews 17: 155-161, 1998.*
Stancovski et al, Proceedings of the National Academy of Science USA 88: 8691-8695, 1991.*
Riemer et al, Mol. Immunol. 42: 1121-1124, 2005.*
Goon et al., Eur Arch Otorhinolaryngol 265: 147-151, Feb. 2008.*
Rahbar et al., Ann Otol Rhino Laryngol 114(4): 289-95, Apr. 2005.*
Kourlas et al., Clinical Therapeutics 29(9): 1850-1861, 2007.*
"Supplement: Assessing the Burden of HPV-Associated Cancers in the United States," Table of Contents, Cancer, 113(S10):2837-3057 (2008).
Amin, "Thyrohyoid approach for vocal fold augmentation," Ann. Otol. Rhinol. Laryngol., 115:699-702 (2006).
Aurelian and Burnett, "Current understanding of herpes simplex virus-associated erythema multiforme," Exp. Rev. Derm., 3(4):491-499 (2008).
Burns et al., "532 nm pulsed potassium-titanyl-phosphate laser treatment of laryngeal papillomatosis under general anesthesia," Laryngoscope, 117(8):1500-1504 (2007).
De Clercq, "Acyclic nucleoside phosphonates in the chemotherapy of DNA virus and retrovirus infections," Intervirology, 40(5-6):295-303 (1997).
Dickens et al., "Human papillomavirus 6, 11, and 16 in laryngeal papillomas," J. Pathol., 165(3):243-246 (1991).
El-Bitar and Zalzal, "Powered instrumentation in the treatment of recurrent respiratory papillomatosis: an alternative to the carbon dioxide laser," Arch. Otolaryngol. Head. Neck. Surg., 128(4):425-428 (2002).
Ford et al., "Rigid endoscopy for monitoring indirect vocal fold injection," Laryngoscope, 108:1584-1586 (1998).
Ford, "A multipurpose laryngeal injector device," Otolaryngol Head Neck Surg., 103:135-137 (1990).
Franco et al., "585-nm pulsed dye laser treatment of glottal dysplasia," Ann. Otol. Rhinol. Laryngol., 112:751-758 (2003).
Franco et al., "585-nm pulsed dye laser treatment of glottal papillomatosis," Annals of Otology, Rhinology and Laryngology, 111:486-492 (2002).
Fung et al., "The International Intravitreal Bevacizumab Safety Survey: using the internet to assess drug safety worldwide," Br. J. Opthtalmol. 90:1344-1349 (2006).
Gallagher and Derkay, "Recurrent respiratory papillomatosis: update 2008," Curr. Opin. Otolaryngol. Head Neck Surg., 16(6):536-542 (2008).
Gillison and Lowy, "A causal role for human papillomavirus in head and neck cancer," Lancet, 363 (9420):1488-1489 (2004).
Gillison, "Human papillomavirus-associated head and neck cancer is a distinct epidemiologic, clinical, and molecular entity," Semin. Oncol., 31(6):744-754 (2004).
Goon et al., "Recurrent respiratory papillomatosis: an overview of current thinking and treatment," Eur. Arch. Otorhinolaryngol., 265:147-151 (2008).
Gross, "Therapy of human papillomavirus infection and associated epithelial tumors," Intervirology, 40(5-6):368-377 (1997).

(Continued)

*Primary Examiner* — Phuong Huynh
(74) *Attorney, Agent, or Firm* — Fish & Richardson P.C.

(57) ABSTRACT

Described are methods of treating virus-associated lesions using administration of an anti-angiogenic compound, or a combination of angiolytic or ablative therapy and administration of an anti-angiogenic compound.

29 Claims, 3 Drawing Sheets

(56) References Cited

OTHER PUBLICATIONS

Kleinsasser, "Laryngeal Papillomas in Children," in *Microlaryngoscopy and Endolaryngeal Microsurgery*, W.B. Suanders: Philadelphia, pp. 70-75 (1968).

Lee and Rosen, "Efficacy of cidofovir injection for the treatment of recurrent respiratory papillomatosis," J. Voice, 18(4):551-556 (2004).

Lee and Smith, "Recurrent respiratory papillomatosis: pathogenesis to treatment," Curr. Opin. Otolaryngol. Head Neck Surg., 13(6):354-359 (2005).

Lynch and Cheng, "Bevacizumab for neovascular ocular diseases," Ann. Pharmacother., 41:614-625 (2007).

Munoz et al., "Epidemiologic classification of human papillomavirus types associated with cervical cancer," New Engl. J. Med., 348(6):518-527 (2003).

Rahbar et al., "Role of vascular endothelial growth factor A in children with acquired airway stenosis," Ann. Otol. Rhinol. Laryngol., 116(6):430-435 (2007).

Rahbar et al., "Role of vascular endothelial growth factor-A in recurrent respiratory papillomatosis," Ann. Otol. Rhinol. Laryngol., 114(4):289-295 (2005).

Ryerson, "Burden of Potentially Human Papillomavirus-associated Cancers of the Oropharynx and Oral Cavity in the US, 1998-2003," Assessing the Burden of HPV-Associated Cancers in the United States (Supplement to Cancer), 2901-2909 (2008).

Silverman and Pitman, "Current diagnostic and management trends for recurrent respiratory papillomatosis," Curr. Opin. Otolaryngol. Head Neck Surg., 12(6):532-537 (2004).

Strong et al., "Recurrent respiratory papillomatosis: management with the CO2 laser," Otol. Rhinol. Laryngol., 85:508-516 (1976).

Wiatrak, "Overview of recurrent respiratory papillomatosis," Curr. Opin. Otolaryngol. Head Neck Surg., 11(6):433-441 (2003).

Zeitels and Sataloff, "Phonomicrosurgical resection of glottal papillomatosis," J. Voice, 13:123-127 (1999).

Zeitels and Vaughan, "A submucosal true vocal fold infusion needle," Otolaryngol. Head Neck Surg., 105:478-479 (1991).

Zeitels et al., "Adduction Arytenopexy: A New Procedure for Paralytic Dysphonia with Implications for Implant Medialization," Ann. Otol. Rhinol. Laryngol. Suppl., 107(suppl 173):2-24 (1998).

Zeitels et al., "Office-based 532-nm pulsed KTP laser treatment of glottal papillomatosis and dysplasia," Ann. Otol. Rhinol. Laryngol., 115:679-685 (2006).

Zeitels et al., "Office-based laryngeal laser surgery with the 532-nm pulsed-potassium-titanyl-phosphate laser," Current Opinion in Otolaryngology & Head & Neck Surgery, 15:394-400 (2007).

Zeitels et al., "Office-based treatment of glottal dysplasia and papillomatosis with the 585-nm pulsed dye laser and local anesthesia," Ann. Otol. Rhinol. Laryngol., 113(4):265-276 (2004).

Zeitels et al., "Photoangiolytic Laser Treatment of Early Glottic Cancer: A New Management Strategy," Annals of Otology, Rhinology, & Laryngology, 117(sup 199):1-24 (2008).

Zeitels et al., "Pulsed angiolytic laser treatment of ectasias and varices in singers," Ann. Otol. Rhinol. Laryngol., 115:571-580 (2006).

Zeitels, "Office-based and microlaryngeal applications of a fiber-based thulium laser," Ann. Otol. Rhinol. Laryngol., 115:891-896 (2006).

Zeitels, "Premalignant Epithelium and Microinvasive Cancer of the Vocal Fold: The Evolution of Phonomicrosurgical Management," Laryngoscope, 105(suppl 67):1-51 (1995).

Zeitels, "Universal modular glottiscope system: the evolution of a century of design and technique for direct laryngoscopy," Ann. Otol. Rhinol Laryngol. Suppl., 108(suppl 179):2-24 (1999).

Zeitels, *Papillomatosis*, In "Atlas of phonomicrosurgery and other endolaryngeal procedures for benign and malignant disease," San Diego: Singular, pp. 119-131 (2001).

Zhu et al., "Risks of proteinuria and hypertension with bevacizumab, an antibody against vascular endothelial growth factor: systematic review and meta-analysis," Am. J. Kidney Dis., 49:186-193 (2007).

Zweig et al., "Histopathology of tissue samples removed using the microdebrider technique: implications for endoscopic sinus surgery," Am. J. Rhinol., 14(1):27-32 (2000).

Chun et al., "Combination of laser photocoagulation and intravitreal bevacizumab (Avastin) for aggressive zone I retinopathy of prematurity," Graefe's Archive for Clinical and Experimental Ophthalmology 245(11)1727-1730 (2007).

Gerten, "Bevacizumab (avastin) and argon laser to treat neovascularization in corneal transplant surgery," Cornea, 27(10):1195-1199 (2008).

Nagel et al., "Treatment of respiratory papillomatosis a case report on systemic treatment with bevacizumab," Pneumologie, 63(7):387-389 (2009).

Phung et al., "Can the wound healing response of human skin be modulated after laser treatment and the effects of exposure extended? Implications on the combined use of the pulsed dye laser and a topical angiogenesis inhibitor for treatment of port win stain birthmarks," Lasers in Surgery and Medicine, 40(1):1-5 (2008).

Zeitels et al., "Microlaryngoscopic and office-based injection of bevacizumab (Avastin) to enhance 532-nm pulsed KTP laser treatment of glottal papillomatosis," The Annals of Otology, Rhinology & Laryngology, 201:1-13 (2009).

Office Action issued in JP2011-549277 on Jan. 28, 2014 with English cover letter (5 pages).

"Peregrine's Anti-Angiogenesis Antibody, 2C3, Shown to Inhibit Tumor Growth by 75%," Feb. 3, 2003; from http://ir.peregrineinc.com/releasedetail.cfm?ReleaseID=266221.

Armstrong et al., Initial Results From the National Registry for Juvenile-Onset Recurrent Respiratory Papillomatosis. Arch Otolaryngol Head Neck Surg. 1999;125(7):743-8.

Best et al., Safety and dosing of bevacizumab (avastin) for the treatment of recurrent respiratory papillomatosis. Ann Otol Rhinol Laryngol. Sep. 2012;121(9):587-93, abstract.

Brekken et al., Selective Inhibition of Vascular Endothelial Growth Factor (VEGF) Receptor 2 (KDR/Flk-1) Activity by a Monoclonal Anti-VEGF Antibody Blocks Tumor Growth in Mice, Cancer Research, 60:5117-5124 (2000).

CATT Research Group, Martin et al., Ranibizumab and bevacizumab for neovascular age-related macular degeneration. N Engl J Med. 364(20):1897-1908 (2011), Abstract.

Derkay and Wiatrak, Recurrent Respiratory Papillomatosis: A Review. Laryngoscope, 118:1236-1247, 2008.

DeVoti et al., "Immune Dysregulation and Tumor-Associated Gene Changes in Recurrent Respiratory Papillomatosis: A Paired Microarray Analysis," Mol. Med., 14(9-10):608-617 (2008).

Johnson and Mendez, "Attacking Vocal Cord Disease With Cancer Drug," May 18, 2009, from http://abcnews.go.com/WN/story?id=7700000&page=1.

Johnson and Trachtenberg, "Medical Miracle: Opera Singer's Lost Voice Returns," Dec. 18, 2009; from, http://abcnews.go.com/GMA/OnCall/opera-singers-lost-voice-returns-devastating-diagnosis/story?id=9364014.

LaPook, "Surgeon repairs voices of children and superstars," Nov. 14, 2012; from http://www.cbsnews.com/8301-18563_162-57550008/surgeon-repairs-voices-of-children-and-superstars/.

Maturo and Hartnick, Use of 532-nm pulsed potassium titanyl phosphate laser and adjuvant intralesional bevacizumab for aggressive respiratory papillomatosis in children: initial experience. Arch Otolaryngol Head Neck Surg. Jun. 2010;136(6):561-5. doi: 10.1001/archoto.2010.81, abstract.

McClay et al., Recurrent Respiratory Papillomatosis: Surgery Treatment & Management, Dec. 5, 2001, http://emedicine.medscape.com/article/865758-treatment.

McClay et al., "Recurrent Respiratory Papillomatosis: Surgery," Dec. 5, 2011, at http://emedicine.medscape.com/article/865758-overview.

Reeves et al., National Registry for Juvenile-Onset Recurrent Respiratory Papillomatosis. Arch Otolaryngol Head Neck Surg. 2003;129(9):976-982.

Rogers et al., Use of adjuvant intralesional bevacizumab for aggressive respiratory papillomatosis in children. JAMA Otolaryngol Head Neck Surg. Aug. 1, 2013;139(8):811-6, abstract.

(56) References Cited

OTHER PUBLICATIONS

RRP Taskforce Recommendations, Cidofovir for Recurrent Respiratory Papillomatosis (RRP): A Plea for Caution (2005), from http://rrpwebsite.org/index.cfm/category/334/cidofovir-by-rrp-taskforce-cautionary.cfm.
Saleh, Complications of treatment of recurrent laryngeal papillomatosis with the carbon dioxide laser in children, The Journal of Laryngology & Otology, 106(8):715-718 (1992), Abstract.
Sullivan et al., r84, a Novel Therapeutic Antibody against Mouse and Human VEGF with Potent Anti-Tumor Activity and Limited Toxicity InductionPLoS ONE. 5(8):e12031 (2010), abstract.
Voice Health Institute: News (http://www.voicehealth.org/news.php), 2013.
Wang, "Celebrex (Celecoxib) Treatment of Laryngeal Papilloma," Boston University, ClinicalTrials.gov (http://clinicaltrials.gov/ct2/show/NCT00592319?cond=%22Papilloma%22&rank=2) (2012).
Yu et al., A Humanized Anti-VEGF Rabbit Monoclonal Antibody Inhibits Angiogenesis and Blocks Tumor Growth in Xenograft Models, PLoS One, 5(2):e9072 (2010).
Zeitels et al., Local injection of bevacizumab (Avastin) and angiolytic KTP laser treatment of recurrent respiratory papillomatosis of the vocal folds: a prospective study. Ann Otol Rhinol Laryngol. Oct. 2011;120(10):627-34, abstract.
Zeitels et al., Microlaryngoscopic and office-based injection of bevacizumab (Avastin) to enhance 532-nm pulsed KTP laser treatment of glottal papillomatosis. Ann Otol Rhinol Laryngol Suppl. Sep. 2009;201:1-13, abstract.
Zhang et al., A monoclonal antibody that blocks VEGF binding to VEGFR2 (KDR/Flk-1) inhibits vascular expression of Flk-1 and tumor growth in an orthotopic human breast cancer model. Angiogenesis. 5(1-2):35-44 (2002), Abstract.
English Translation of Office Action issued in JP2011-549277 issued on Aug. 19, 2014 (2 pages).
Office Action issued in EP10739153.4 on Jul. 17, 2013 (5 pages).
English Translation of Office Action issued in CN201080009616.5 on Jun. 5, 2014 (7 pages).

* cited by examiner

FIGURES 1A-F

METHODS OF TREATING VASCULAR LESIONS

CLAIM OF PRIORITY

This application is a 371 application of International Application No. PCT/US2010/023295, filed on Feb. 5, 2010, and claims the benefit of the following U.S. Provisional Patent Applications: Ser. No. 61/150,476, filed on Feb. 6, 2009; Ser. No. 61/151,158, filed on Feb. 9, 2009; and Ser. No. 61/167,331, filed on Apr. 7, 2009, the entire contents of all of which are hereby incorporated by reference.

TECHNICAL FIELD

This invention relates to methods of treating vascular lesions such as virus-associated lesions using anti-angiogenic compounds, or a combination of angiolytic or ablative laser therapy and administration of an anti-angiogenic compound.

BACKGROUND

Phonatory mucosal lesions, such as virus-associated lesions (e.g., papillomas) are often treated with surgical treatment, including microlaryngeal cold instruments (e.g., microscissors, microforceps (Kleinsasser, "Laryngeal Papillomas in Children," in *Microlaryngoscopy and Endolaryngeal Microsurgery*. 1968, W. B. Saunders: Philadelphia. pp. 70-75; Zeitels and Sataloff, J. Voice, 13:1323-127 (1999); Zeitels,
   Atlas of Phonomicrosurgery and Other Endolaryngeal Procedures for Benign and Malignant Disease. 2001, Singular: San Diego.), and microdebriders (El-Bitar and Zalzal, Arch. Otolaryngol. Head. Neck. Surg. 128(4):425-8 (2002); Zweig et al., Am J Rhinol, 14(1):27-32 (2000)) ablative lasers (e.g., carbon dioxide (Strong et al., Otol. Rhinol. Laryngol. 85:508-516 (1976)) and Thulium (Zeitels, Ann Otol Rhinol Laryngol, 115:891-896 (2006)). Most recently, photoangiolytic lasers (e.g., the 532-nm pulsed potassium titanyl phosphate (KTP) laser (Burns et al., Laryngoscope, 117(8):1500-1504 (2007); Zeitels et al., Current Opinion in Otolaryngology & Head & Neck Surgery, 15:394-400 (2007); Zeitels et al., Aim Otol Rhinol Laryngol, 115:679-685 (2006); Zeitels et al., Ann Otol Rhinol Laryngol, 115:571-580 (2006); Zeitels et al., Annals of Otology, Rhinology, & Laryngology, 117(supp 199):1-24 (2008)) or the 585-nm pulsed dye laser (PDL) (Franco et al., Ann Otol Rhinol Laryngol, 112:751-758 (2003); Franco et al., Annals of Otology, Rhinology and Laryngology, 111:486-492 (2002); Zeitels, *Papillomatosis*. In "Atlas of phonomicrosurgery and other endolaryngeal procedures for benign and malignant disease" (pp. 119-131). San Diego: Singular (2001); Zeitels et al., Ann Otol Rhinol Laryngol, 113(4):265-276 (2004)) have emerged as the best surgical option to treat these disorders. Photoangiolytic lasers are especially valuable in precisely treating laryngeal papillomatosis due to the ability to selectively target the intralesional angiogenic microcirculation of the lesions. However, no surgical approach reliably prevents recurrence, even when coupled with adjuvant therapy, e.g., with antiviral compounds such as cidofovir (De Clercq, Intervirology. 40(5-6):295-303 (1997); Gross, Intervirology. 40(5-6):368-77 (1997)). Furthermore, adjuvant treatment with antiviral agents have been reported to cause irreparable vocal cord mucosal scarring and permanent hoarseness (Lee and Rosen, J Voice, 18(4):551-556 (2004)).

SUMMARY

As described herein, administration of an anti-angiogenic agent, e.g., an anti-VEGF compound, e.g., Avastin™ (bevacizumab), alone or in combination with cytoreductive treatment, e.g., photoangiolytic laser treatment, e.g., pulsed-KTP laser photoangiolysis, enhances treatment of angiogenic viral lesions, e.g., glottal papillomatosis. Therefore, the present invention provides methods for the treatment of angiogenic lesions including virus-associated lesions using administration of an anti-angiogenic compound, optionally in conjunction with cytoreductive treatment, e.g., cold-instrument surgical, cryotherapy, radiofrequency, electrosurgical, and/or laser debulking of the angiogenic lesions.

Thus, in one aspect, the invention provides methods for locally treating (e.g. injecting) a neoplasm or lesion with a vascular component within the intraparenchymal organs, mucosa or skin, e.g., viral-induced vascular lesions, e.g., epithelial vascular lesions, in a subject. The methods include administering to the subject an amount of an inhibitor of angiogenesis, and as appropriate exposing the lesion to a cytoreductive treatment sufficient to substantially debulk the lesion. In some embodiments, the lesion is a papilloma caused by human papilloma virus (HPV). In some embodiments, the inhibitor of angiogenesis is an anti-VEGF compound., e.g., an anti-VEGF antibody, e.g., bevacizumab. The inhibitor of angiogenesis can be administered to the subject systemically or locally, e.g., by local administration to the lesion or to tissues adjacent to the lesion. In some embodiments, the optional cytoreductive treatment is provided by a laser selected from the group consisting of a $CO_2$ laser, an Nd:YAG laser, a Thulium laser and an Er,Cr:YSGG laser; in some embodiments, the cytoreductive treatment is provided by a laser selected from the group consisting of a 532-nm pulsed potassium titanyl phosphate (KTP) laser or a 585-nm pulsed dye laser (PDL). In some embodiments, the optional cytoreductive treatment is provided by cold instruments, e.g., microscissors and microforceps or a microdebrider. In some embodiments, the optional cytoreductive treatment is an ablative tissue treatment, e.g., provided by cryotherapy, radiofrequency, or electrocautery.

In some embodiments, the lesion is an epithelial tumor, and/or is present on the skin of the subject. In some embodiments, the lesion is can be present on any mucosal tissue of the subject, or in an organ, e.g., in the respiratory tract, genitourinary tract, or in the upper or lower digestive tract (i.e., from the oral cavity to rectum). In some embodiments, the lesion is present on an internal organ (e.g., the spleen, lung, liver or kidney).

In some embodiments, the subject is suffering from recurrent respiratory papillomatosis.

In some embodiments, the methods further include administering one or more additional doses of the inhibitor of angiogenesis, e.g., at subsequent times. The methods described herein can also be performed more than once, e.g., in the event of recurrence of a lesion.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is a photograph showing bilateral recurrent respiratory papillomatosis in glottis of 40-year-old classical vocalist. He had undergone multiple 532-nm pulsed KTP angiolytic laser procedures, which preserved phonatory mucosal pliability but did not prevent disease recurrence.

FIG. 1B is a photograph showing the same examination as in 1A, during adduction.

FIG. 1C is a photograph showing an office-based injection of 7.5 mg of bevacizumab given to the same patient as shown in FIG. 1A in subepithelial superficial lamina propria of right vocal fold. Infusion has visually displaced right-sided disease caudally.

FIG. 1D is a photograph showing the use of office-based 532-nm pulsed KTP photoangiolysis done on disease bilaterally, on the same day (and in the same patient) as 1C, after bevacizumab injection. Note white eschar in laser-treated regions and that 0.3-mm fiber (arrow) is in contact with exophytic lesion within anterior commissure region of left vocal fold.

FIG. 1E is a photograph showing the same patient's vocal folds during abduction (opening). Laser procedures were discontinued after second injection. Patient subsequently underwent total of 3 more injections. It has been 6 months since last injection, and active disease is not seen.

FIG. 1F is a photograph showing the same view as in 1E during adduction (closing); there are substantial secretions noted in glottal introitus consistent with reflux history.

FIG. 1B shows a photograph taken during an office-based injection of bevacizumab.

DETAILED DESCRIPTION

Figure 2A:
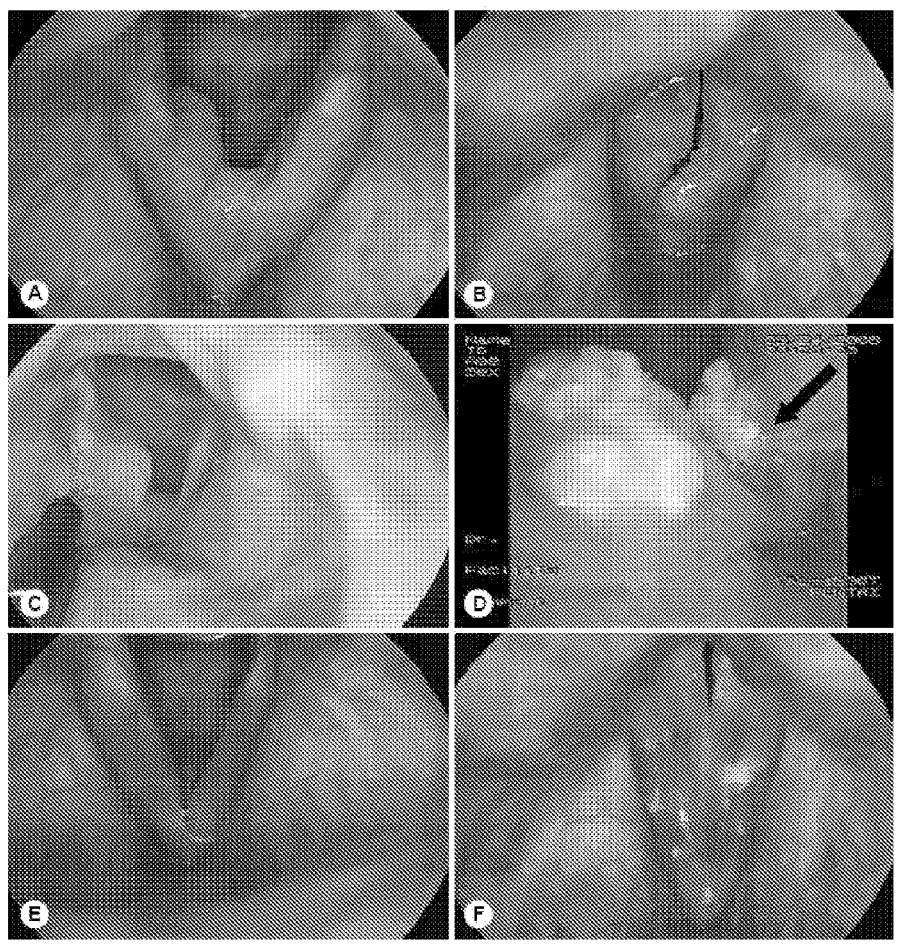
FIGS. 2A and 2B are photographs showing the vocal folds of a different patient from that shown in FIGS. 1A-F, before (1A, showing severe obstruction of the airway) and after (1B) treatment using the methods described herein.

At least in part, the present invention is based on the discovery that the administration of an anti-angiogenic compound, alone or in combination with a surgical removal (e.g., using cold instruments, electrocautery, radiofrequency, laser, or cryotherapy) is useful in the treatment of chronic virus-associated angiogenic microvascular lesions, providing improved clinical outcome and reduced likelihood of recurrence. Using an anti-angiogenic compound in combination with an angiolytic laser is especially efficacious.

Methods of Treatment

The methods described herein include the administration of an anti-angiogenic agent, and optionally the use of a cytoreductive treatment sufficient to substantially debulk (i.e., reduce the size of) the lesion in combination with administration of an anti-angiogenic agent.

The methods described herein include methods for the treatment of mucosal, skin, or intraparenchymal organ lesions associated microvascular-related growth. In some embodiments, this includes infection with a virus such as the disorder papillomatosis, e.g., respiratory papillomatosis. In some embodiments, the methods include administering a therapeutically effective amount of an anti-angiogenic compound as described herein, optionally in conjunction with a laser angiolytic treatment, to a subject who is in need of, or who has been determined to be in need of, such treatment.

As used in this context, to "treat" means to ameliorate at least one symptom of the disorder. For example, treatment using the methods described herein can result in a reduction in size or number of lesions and a delay or prevention (i.e., a reduction in the likelihood) of recurrence. "Prevention" as used herein need not prevent the recurrence 100% in all cases, but is a significant reduction in the likelihood of recurrence.

The treatments described herein can be administered one or more times per week including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with the methods described herein can include a single treatment or a series of treatments.

Cytoreductive Treatments

A number of suitable cytoreductive treatments are known in the art, e.g., photoangiolytic lasers, ablative lasers, electrosurgery, cryosurgery, radiofrequency, and cold-instrument surgical procedures.

Thus, the methods described herein can include the use of known photoangiolytic laser treatments, which use selective hemoglobin-absorbing focused laser light to destroy lesions. This includes the 532-nm pulsed potassium titanyl phosphate (KTP) laser or the 585-nm pulsed dye laser (PDL). Such methods are known in the art and described for use in microlaryngeal surgery (see, e.g., Zeitels, "Papillomatosis," in *Atlas of Phonomicrosurgery and Other Endolaryngeal Procedures for Benign and Malignant Disease.* 2001, Singular: San Diego. p. 119-131; Burns et al., Laryngoscope, 2007. 117(8): 1500-4; Franco et al., Ann. Rhinol Laryngol., 2002; 111:486-492) with general anesthesia and as an office-based procedure (Zeitels et al., Ann. Otol. Rhinol. Laryngol. 2004 April; 113(4):265-76; Zeitels et al., Ann Otol. Rhinol. Laryngol. 2006; 115:679-685; Zeitels et al., Curr. Op. Otolaryngol. Head Neck Surg. 2007; 15:394-400) with topical local anesthesia. In some embodiments, the photoangiolytic laser treatments comprise exposing the lesion to one or a plurality of pulses from an angiolytic laser source. In some embodiments, angiolytic laser treatment is applied until blanching of the lesion (e.g., a papilloma) is observed.

In some embodiments, the cytoreductive treatment is an ablative laser treatment, e.g., using a $CO_2$ laser, an Nd:YAG laser, or an Er,Cr:YSGG laser, as are known in the art.

In other embodiments, the cytoreductive treatment is a surgical treatment employing cold instruments (Kleinsasser, "Laryngeal Papillomas in Children," in *Microlaryngoscopy and Endolaryngeal Microsurgery.* 1968, W. B. Saunders:

Philadelphia. p. 70-75, Zeitels and Sataloff, J. Voice, 13:1323-127 (1999); Zeitels, 2001, supra) or ablative lasers such as the Carbon Dioxide (Zeitels, 2001, supra; Strong et al., Otol. Rhinol. Laryngol. 85:508-516 (1976)) or Thulium lasers (Zeitels et al., Ann Otol Rhinol Laryngol. 115(12): 891-6 (2006)). Phonomicrosurgery can also be used, see, e.g., Zeitels and Sataloff, J. Voice. 13(1):123-7 (1999).

In general, any treatment is applied until sufficient debulking or removal is achieved, i.e., a significant diminution in the size of the lesion. In some embodiments, a laser treatment is applied until blanching of the lesion (e.g., a papilloma) is observed.

For further information, see, e.g., Silverman and Pitman, Curr Opin Otolaryngol Head Neck Surg. 12(6):532-7 (2004); Gallagher and Derkay, Curr Opin Otolaryngol Head Neck Surg. 16(6):536-42 (2008); Lee and Smith, Curr Opin Otolaryngol Head Neck Surg. 13(6):354-9 (2005); and Goon et al., Eur Arch Otorhinolaryngol. 265(2):147-51 (2008), Epub 2007 Nov. 29.

Anti-Angiogenic Agents

A number of anti-angiogenic agents are known in the art that can be used in the methods described herein. For example, anti-angiogenic agents can include angiostatin (e.g., plasminogen fragment), anti-angiogenic antithrombin III (aaATIII), canstatin, cartilage-derived inhibitor (CDI), CD59 complement fragment, endostatin (e.g., collagen XVIII fragment), fibronectin fragment, gro-beta, heparinases, heparin and fragments thereof (e.g., hexasaccharide fragment), human chorionic gonadotropin (hCG), interferon alpha/beta/gamma, interferon inducible protein (IP-10), IL-12, kringle 5 (plasminogen fragment), metalloproteinase inhibitors, 2-niethoxyestradiol, PEDF, placental ribonuclease inhibitor, platelet factor-4, prolactin 16 kD fragment, proliferin-related protein, retinoids, tetrahydrocortisol-S, thrombospondin, transforming growth factor-beta, tumistatin, vasculostatin and vasostalin (calreticulin fragment), fumagillin, non-glucocorticoid steroids, and antibodies to one or more angiogenic peptides such as alpha-FGF, bFGF, VEGF, IL-8, and GM-CSF. A number of other anti-angiogenic agents are described in U.S. Pat. No. 7,422,738, incorporated herein by reference in its entirety.

In some embodiments, the anti-angiogenic agent blocks VEGF signaling. There are at least three methods to block VEGF signaling that have been used to date. The first method is to inhibit VEGF (e.g. VEGF-A, -B, -C, -D, PGF) and/or VEGFR (e.g. VEGFR-1, -2, -3) using antibodies. Examples include: Avastin ™ (bevacizumab), a recombinant humanized monoclonal antibody that binds to VEGF-A and prevent interaction of VEGF-A to VEGFR-1 and VEGFR-2 (see, e.g., Presta et al., Cancer Res. 57: 4593-4599 (1997); Hurwitz et al., N. Engl. J. Med. 350:2335-2342) (2004); 2C3, a mouse monoclonal antibody against VEGF-A (Zhang et al., Angiogenesis. 5:35-44 (2002); Brekken et al., Cancer Res. 58: 1952-9 (1998)); IMC-1121B, a human monoclonal antibody against VEGFR-2 (Rockwell and Goldstein, U.S. Pat. No. 6,811,779); CDP-791, PEGylated, humanized di-Fab fragment that binds to VEGFR-2 (Ton et al., Clin. Cancer Res. 13:7113-711 (2007)). Lucentis ™ (ranibizumab) is a recombinant humanized monoclonal antibody that binds to VEGF-A, but its approved usage is for treatment of patients with neovascular age-related macular degeneration (available from Genentech).

A second method uses protein kinase inhibitors to inhibit VEGFR (e.g. VEGFR-1, -2, -3). At least two known FDA-approved small molecule inhibitors are on the market: Sutent™ (sunitinib) (Goodman et al., Clin. Cancer Res. 13:1367-1373 (2007)) and Nexavar™ (sorafenib) (Kane et al., Clin. Cancer Res. 12:7271-8 (2006)). Other kinase inhibitors include, but are not limited to: Vatalanib (PTK787/ZK222584) which inhibits VEGFR-1, -2, and -3 (Wood et al., Cancer Res. 60:2178-2189 (2000)); CEP-7055, inhibitor of VEGFR-1, -2, and -3 (Ruggeri et al., Cancer Res. 63: 5978-5991(2003)); CP-547,632, inhibitor of VEGFR-2 and FGF (Beebe et al., Cancer Res. 63: 7301-7309 (2003)).

A third method uses the so-called "VEGF-trap," i.e., soluble hybrid VEGF receptors that bind to the VEGF ligand and prevent binding to VEGFRs (Holash et al., Proc. Natl. Acad. Sci. 99:11393-11398 (2002)).

In some embodiments, the anti-angiogenic agent is an anti-Vascular Endothelial Growth Factor (VEGF) agent, e.g., an anti-VEGF antibody or antigen-binding portions thereof (such as Fv, Fab, or scFv portions) to inhibit VEGF binding to KDR and/or flt receptors, e.g., Avastin® (Bevacizumab). Avastin™ is a recombinant humanized monoclonal IgG1 antibody that binds to and inhibits the biologic activity of human VEGF both in vitro and in vivo. Bevacizumab contains human framework regions and the complementarity-determining regions of a murine antibody that binds to VEGF (Presta et al., Cancer Res 57:4593-9 1997). Avastin™ is available from Genentech (South San Francisco, CA). See also: Schlaeppi and Wood, Cancer and Metastasis Rev. 1999; 18:473-481; U.S. Pat. Nos. 7,169,901; 7,056,509; and 7,297,334; U.S. Pat. Pub. No. 20020032315; 20080187966; and 20090010883; and PCT No. WO 94/10202. In some embodiments, the antibody binds specifically to VEGF and block binding to VEGFR1, to VEGFR2, or block binding to both VEGFR1 and VEGFR2.

Other anti-VEGF agents include VEGF antagonists, which could compete with VEGF for binding to KDR and/or flt receptors (e.g. soluble truncated forms of flt receptor, which bind to VEGF, as described, for example, in WO 94/21679); and tyrosine kinase inhibitors.

In some embodiments, the anti-angiogenic agent is not an inhibitor of cyclooxygenase (COX)-2, e.g., is not celecoxib (4-(5-(4-Methylphenyl)-3-(trifluoromethyl)-1H-pyrazol-1-yl)benzenesulfonamide, CELEBREX™). The anti-angiogenic agent is also not interferon, Indole-3-carbinol, Methotrexate, or Cidofovir.

In some embodiments, the anti-angiogenic is a small interfering RNA (siRNA) targeting VEGF or a VEGFR, e.g., Bevasiranib (Cand5; OPKO Health; a modified siRNA targeting all VEGF-A splice forms) or AGN-745 (Sirna-027; Merck; a chemically modified siRNA targeting VEGFR-1), see, e.g., de Fougerolles, Human Gene Therapy 19:125-132 (2008); and anti-VEGF aptamers (e.g., Macugen (pegaptanib; OSI Pharmaceuticals, a pegylated anti-VEGF-A aptamer), see, e.g., Tremolada et al. Am. J. Cardiovasc. Drugs 7:393-398 (2007)).

Delivery

The anti-angiogenic agents can be administered, e.g., systemically or locally to the tissue to be treated. Examples of routes of administration include parenteral, e.g., intravenous, intramucosal, submucosal, intradermal, subcutaneous, transmucosal (e.g., inhalation), oral, transdermal (topical), and rectal administration. For example, the anti-angiogenic agents can be administered by injection into or around the lesion.

For example, anti-angiogenic agents can be injected within or just below the surface of a skin or mucosal lesion, benign or malignant neoplasm, or inflammatory disease. Alternatively they may be administered intra-arterially either by angiography or by direct surgical access to arteries feeding an area of pathology. These intralesional and/or sublesional injections, or intra-arterial injections may lead to complete involution, partial recession or diminution in volume. These local and regional injections of an antiangiogenesis drug may be accompanied by mucosal ablative procedures such as cold instruments (e.g. forceps, scissors, automated debriders), lasers, electrocautery, radiofrequency, and/or cryotherapy.

In some embodiments, intra-arterial, intralesional and sub-lesional injections of an anti-angiogenic agent into solid tumors or mucosal carcinomas can be used to enhance other cancer treatments such as radiotherapy, cytotoxic ablative chemotherapy, or even surgery. In that latter model, the anti-angiogenesis agent might be used at the time of resection of a mucosal tumor to enhance local control. If there is field dysplasia at the perimeter of the cancer, and resection of the entirety of that region including the dysplasia would lead to extreme morbidity due to the encompassing of the entire zone of precancerous and cancerous tissue, the anti-angiogenesis agent could be injected into the cancer as well as administered to the surrounding perimeter of dysplasia. This could diminish morbidity associated with wide-margin complete removal of soft tissue until the margin is completely normal. This scenario is not uncommon in aerodigestive tract and genitourinary tumors. This scenario of dysplastic margins of condemned mucosa or dermis adjacent to invasive cancer is commonplace in aerodigestive and genitourinary tracts as well as skin.

In some embodiments of methods for the use of anti-angiogenesis agents in the treatment of mucosal diseases, the agents are applied to mucosal or skin surfaces locally and topically. By altering the delivery of the anti-angiogenesis agent, it might be used to topically treat diseases of the skin, aerodigestive tract or genitourinary systems. With the example of papilloma in the airway, the anti-angiogenesis agent might be used as an inhaler to be topically absorbed through the mucosa into the lesion. The antiangiogenesis agent may also be administered in a cream to be applied directly to the skin for inflammatory diseases, precancerous dysplasia or cancer regions. It may also be placed topically by a clinician to skin or mucosal surfaces such as the larynx, pharynx, bladder, and cervix.

Formulations—Controlled Release Formulations

Pharmaceutical compositions are typically formulated to be compatible with its intended route of administration. Methods of formulating suitable pharmaceutical compositions are known in the art, see, e.g., the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

One strategy to enhance the effectiveness of anti-angiogenic agents for treating skin or mucosal lesions is to delay the release of the drug to the tissues using a controlled release formulation.

There are a variety of options for enhancing the residence time of the drug in the soft tissues. Delayed release of the anti-angiogenesis agent may be achieved in a variety of manners familiar to those skilled in the art including the use of microspheres or nanoparticles, or embedding the drug in a suitable carrier (such as a tissue expander/filler) that is inert to the local tissues or even possibly beneficial to the local function, such as a biomaterial that will restore vocal cord function. Biodegradable polymers for use in controlled release formulations are known in the art, e.g., for polymeric implants or microcapsules or nano- or micro-spheres, including poly(lactic-co-glycolic acid) PLGA microspheres; D,L-lactic acid oligomer; microcapsules of polylactic acid or copoly(lactic/glycolic) acid; poly(alpha-hydroxy acid) microspheres; Polyanhydride microspheres; Hyaluronic acid hydrogel. See, e.g., Putney and Burke, Nature Biotechnology 16:153-157 (1998); Talmadge, Adv. Drug Del. Rev. 10:247-299 (1993); Cleland and Jones, Pharm. Res. 13:1462-1473 (1996); Tian et al., J. Control. Release, 102(1):13-22 (2005); Grainger, Exp. Op. Biol. Ther. 4(7):1029-1044 (2004); United States Patent Application Pub. Nos. US20050019400; 20070160617; EP0659406B1; EP0765659A1; U.S. Pat. No. 5,980,945; and WO/2006/047279A2; inter alia.

In some clinical circumstances, tissues require augmentation and reconstruction with biomaterials or cellular constructs that restore a function and these biomaterial or cellular constructs may serve as a carrier for anti-angiogenesis agents. In some embodiments there may be a soft tissue deficit after removal of a tumor (e.g., skin) with ongoing local disease growth, and it may be desirable to use a tissue augmentation filler to reduce the appearance of the deficit. The tissue augmentation filler can carry the anti-angiogenic agent. If there is shrinkage of pathology such as mucosal papillomatosis (e.g., in the aerodigestive or genitourinary tracts), skin lesions, or gastroenteral lesions (e.g., angiodysplasia, adenomas, or Barrett's esophagus), the use of such formulations may be particularly desirable.

Delayed or controlled drug delivery may even diminish the amount of mucosal or skin ablation or possibly obviate the need for mucosal ablative procedures. These concepts are illustrated by the example of recurrent respiratory papillomatosis, precancerous dysplasia and cancer in the larynx. In these scenarios, frequent procedures to treat the aforementioned diseases has often lead to substantial loss of the layered microstructure of the vocal fold resulting in phonatory mucosal stiffness. However, despite prior reductive procedures, there is often still ongoing mucosal disease. In this scenario, biomaterial implant or cellular graft might restore the lost subepithelial soft tissues while carrying the anti-angiogenesis agent to involute the disease.

Dosage

Dosage, toxicity and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Although for many of the agents described herein, guidance as to suitable dosages will be available in the art, optimal dosages can also be determined empirically. Data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent (i.e., reduce the likelihood) onset of disease or disease symptoms. An effective amount can be administered in one or more administrations, applications or dosages. A therapeutically effective amount of a composition depends on the composition selected.

Virus-Associated Lesions

Viruses that induce lesions, e.g., tumors, in mammals are quite widespread. In some embodiments, the virus-associated lesions are caused by Human Papillomaviruses (HPV). Other types of viruses that can result in tumors include various RNA viruses as well as herpes viruses. In some embodiments, the lesion is not cancerous.

Although such tumors can also appear in otherwise healthy individuals, people with depressed immune systems, such as those infected with Human Immunodeficiency Virus (HIV), are prone to HPV infections that can cause tumor growth over their entire bodies, resulting in great mental and physical distress to the afflicted individual.

Human Papillomaviruses (HPV)

Human papillomavirus (HPV) is a double-stranded DNA virus with a tropism for epithelial cells, and is associated with tumor formation. Over 100 types of HPV have been identified, sixty-eight of which can induce tumor formation. Some of these HPVs, e.g., types 6 and 11, have been associated with benign tumors, such as common warts, that can occur in mucosal tissues such as the upper gastrointestinal and respiratory tracts as well as the genitourinary tract, and in all age groups (see, e.g., Dickens et al., J Pathol. 165(3):243-6 (1991)). Others have been strongly implicated as etiologic agents in dysplasia and carcinomas in the oral (see, e.g., Gillison, Semin. Oncol. 31(6):744-54 (2004); and Gillison and Lowy, Lancet, 363(9420):1488-9 (2004)) and genital mucosa of the infected mammal; types 16, 18, 31, 33, 35, 39, 45, 51, 52, 56, 58, 59, 68, 73, and 82 are classified as "high risk" HPV. See, e.g., "Supplement: Assessing the Burden of HPV-Associated Cancers in the United States." Cancer. 113 (S10):2837-3057 (2008); Munoz et al., New Engl. J. Med. 348(6):518-527 (2003).

A diagnosis of papillomatosis can be made using standard methods, e.g., ALA-D-Light fluorescence diagnosis.

Recurrent respiratory papillomatosis (RRP) is a common and is in fact the most common benign neoplasm of the larynx in children (approximately 3.96 per 100,000 in the pediatric population) (Wiatrak, Curr. Opin. Otolaryngol. Head Neck Surg. 11(6):433-41 (2003)). Since the both juvenile and adult-onset laryngeal RRP is not conventionally curable, the prevalence is substantially greater than the incidence of new cases annually. Though benign, significant morbidity and occasional mortality is associated with multiple recurrences that can necessitate hospital admission for surgical removal. Dissemination or extension of the growths into the lower airways generally indicates a poorer prognosis. The clinical behavior is variable and lesions can regress, persist and in rare instances, progress to carcinoma if other environmental factors such as smoking or irradiation are involved.

Herpes Simplex Virus

Herpes simplex virus associated erythema multiforme (HAEM) has been described, see, e.g., Aurelian and Burnett, "Current understanding of herpes simplex virus-associated erythema multiforme," Exp. Rev. Derm. August 3(4):491-499 (2008).

Other Virus-Associated Lesions

Other virus-associated lesions include Epstein-Barr virus (EBV)-associated lesions, e.g., EBV-associated hydroa vacciniforme (HV)-like cutaneous lesions.

Non-Viral Lesions

The methods described herein can also be used to treat vascular lesions (e.g., growths or tumors) that may or may not be associated with viral infection. For example, other angiogenic neovascular processes include angiodysplasia of the digestive tract, vascular lesions of the lungs and tracheal bronchial tree, adenomatous polyps throughout the aerodigestive tract, hemangiomas (skin, mucosa, organs), and vasculitides such as Wegener's granulomatosis and Behçet's Disease.

In some embodiments, the lesions are epithelial cell tumors, e.g., non-cancerous epithelial cell tumors.

EXAMPLES

The invention is further described in the following examples, which do not limit the scope of the invention described in the claims.

Example 1

Microlaryngoscopic and Office-Based Injection of AVASTIN™ to Enhance Angiolytic (532 nm KTP Laser, 585 nm Pulsed-Dye Laser) Laser Treatment of Vocal Fold Papillomatosis Photoangiolytic lasers effectively treat glottal papillomatosis by involuting the disease while preserving the pliability of the phonatory mucosa. However, this approach does not reliably prevent recurrence. Therefore, intralesional/sublesional injections of the anti-angiogenic agent bevacizumab (AVASTIN™) were evaluated to determine the effect on disease recurrence and phonatory mucosal pliability/function.

Materials and Methods

A retrospective investigation was performed in a pilot group of 10 patients recalcitrant glottal recurrent respiratory papillomatosis (RRP) who had prior angiolytic laser treatment with established patterns of recurrence. Three of the 10 presented with airway obstruction, and seven of the 10 were being treated for vocal dysfunction associated with frequent disease recurrence. Subepithelial (within the superficial lamina propria) bevacizumab injections (5 to 10 mg) into diseased vocal folds were used along with pulsed KTP laser photoangiolysis treatments 4 to 6 weeks apart until laser ablation was discontinued because it was not necessary to maintain optimal vocal function (FIGS. 1A-F). The patients underwent an initial series of 5 bevacizumab injections of 5 to 10 mg (0.2 to 0.4 mL: 2.5 mg/0.1 the amount of scarring present from prior procedures in the subepithelial superficial lamina propria, and the treatment interval was based in part on practical considerations of patients' travel constraints. Disease assessment was quantified, similar to prior descriptions (Zeitels et al., Ann Otol Rhinol Laryngol, 113:265-76

(2004)), by comparing findings of office laryngoscopic examinations prior and subsequent to the use of bevacizumab.

Bevacizumab injections were done with a microlaryngoscopic infusion needle (Endocraft LLC, Winter Park, Fla.) (Zeitels and Vaughan, Otolaryngol Head Neck Surg, 105: 478-9 (1991)) in the operating room, along with use of the Universal Modular Glottiscope (Endocraft LLC) (Zeitels, Ann Otol Rhinol Laryngol Suppl, 108(suppl 179):2-24 (1999)). The anatomic rationale and procedural technique have been detailed previously (Zeitels, Laryngoscope, 105 (suppl 67):1-51 (1995)). Office-based injections were given with the Ford system (Medtronic Inc, Minneapolis, Minn.) (Ford, Otolaryngol Head Neck Surg, 103:135-7 (1990)) with rigid telescopic guidance (KayPENTAX, Lincoln Park, N.J.; Ford et al., Laryngoscope, 108:1584-6 (1998)) or by Amin's transcervical technique with flexible laryngoscopic control (KayPENTAX) (Amin, Ann Otol Rhinol Laryngol, 115:699-702 (2006)).

The patients underwent standard voice assessments before and after the series of bevacizumab injections. These included videostroboscopy, completion of the Voice-Related Quality-of-Life survey (V-RQOL) (Hogikyan and Sethuraman, J Voice, 13:557-69 (1999)), and objective acoustic and aerodynamic measures of vocal function. Because of its reliance on subjective judgments, observations from videostroboscopic recording were not used as formal data and are only included in the context of discussing the results of vocal function measures. The details of the protocol for obtaining acoustic and aerodynamic measures of vocal function have previously been described (Zeitels et al., Ann Otol Rhinol Laryngol Suppl, 107(suppl 173):2-24 (1998)). When possible, postinjection measures were compared descriptively with preinjection measures and with historical norms (Id.) for individual patients.

Results

Figure 2B:
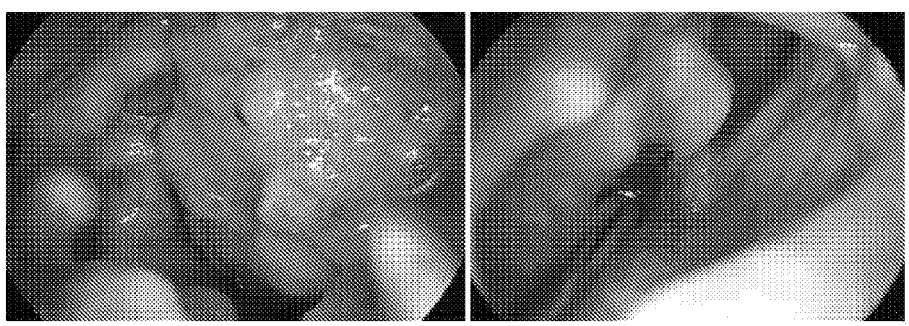

In comparison to their prior glottal recurrence pattern with laser treatment alone, all 10 patients (20 vocal folds) had a more than 90% reduction in recurrence while maintaining or improving mucosal pliability. In addition, seven of the 10 patients (14 of the 20 vocal folds) had complete clinical resolution of the disease. Of those seven patients, four had clinical resolution, and three developed mild recurrence 8 to 10 weeks after the cessation of the bevacizumab injection. However, all three are being maintained with excellent function by use of office injections and without laser ablation. All three of the 10 patients who did not achieve clinical resolution after a series of 5 injections had presented with airway obstruction. Over time, one of the three demonstrated very limited epithelial disease that warranted ongoing injections (see FIGS. 2A-B), but did not require a surgical ablative treatment of the phonatory mucosa. Therefore, four of the 10 cases are at present resolved, and four of the 10 patients have limited recurrent or persistent disease and are injected with bevacizumab at 8- to 12-week intervals, somewhat as in a dystonia model. Two of the 10 patients continue to receive office-based KTP laser treatment combined with bevacizumab injections. These two individuals had initially presented had a tracheotomy. In summary, no patient requires microlaryngeal surgery with general anesthesia, and only two of the 10 patients (four of the 20 vocal folds) still require office-based laser treatment of vocal fold membranes. There were no systemic or local complications as a result of the bevacizumab injections.

Figure 3:
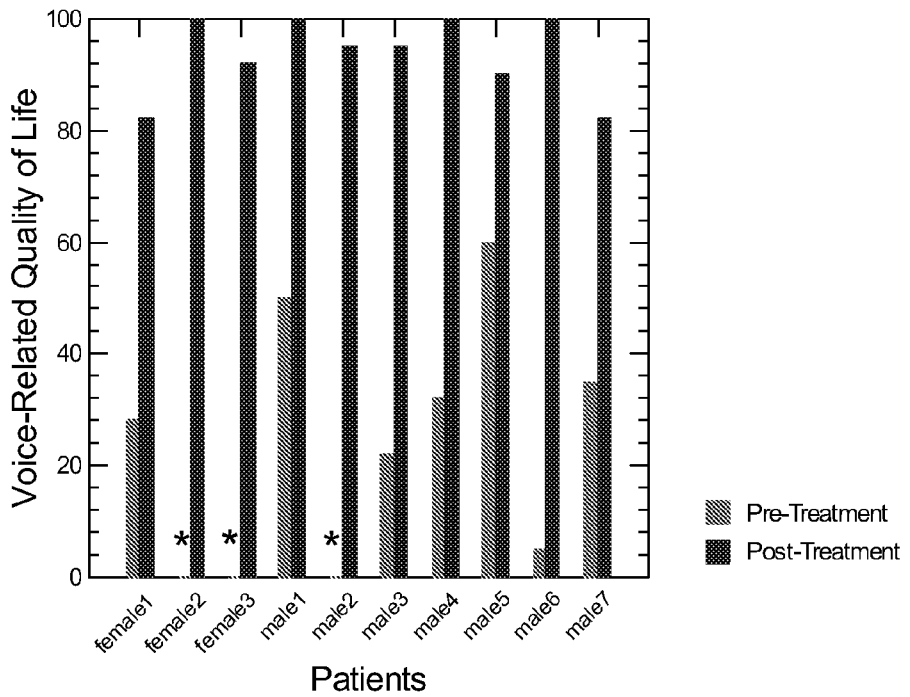
FIG. 3 is a bar graph showing the results from Voice-Related Quality-of-Life (V-RQOL) surveys completed by patients before and after treatment. Higher scores indicate better voice-related quality of life. Asterisk indicates missing data (see Example 1 for explanation).

In this pilot study, a subset of four primary voice assessment measures were utilized to evaluate the impact of the new treatment regimen on vocal function. The measures included the overall V-RQOL score, the average fundamental frequency during reading of a standard passage (F0: vocal pitch), the noise-to-harmonics ratio during sustained vowels (NHR: voice quality), and the ratio between vocal sound pressure level and average subglottal air pressure during production of standard syllable strings (in decibels per centimeter of water: vocal efficiency). FIG. 3 shows results for the V-RQOL survey. On this scale, 0 indicates the lowest voice-related quality of life and 100 indicates the highest voice-related quality of life. Across all patients, the preinjection scores (seven patients) ranged from 28 to 60 and the postinjection scores (10 patients) ranged from 82 to 100. All seven of the patients who completed the V-RQOL before and after treatment displayed dramatic increases in postinjection scores ranging from +30 to +95. Pretreatment scores were not available for patients F2 and F3 (who were initially assessed before we began using the V-RQOL) or for patient M2 (who presented with airway obstruction and was taken emergently to the operating room before any pretreatment voice assessment could be done).

Figure 4:
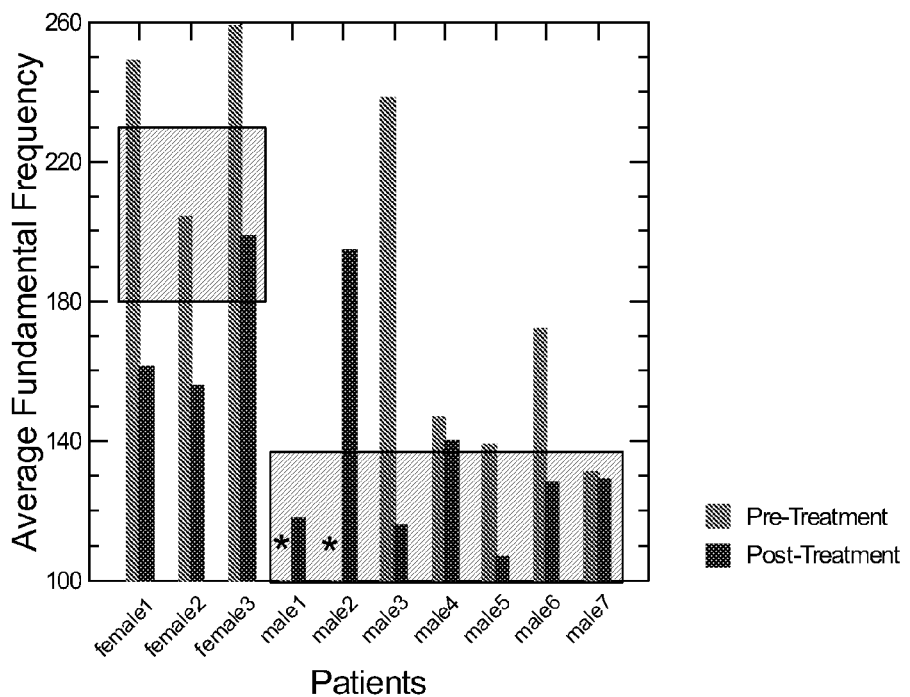
FIG. 4 is a bar graph showing the results from acoustic assessment of average fundamental frequency during reading of standard passage before and after treatment. Cross-hatched areas indicate ranges of normal values for male and female patients separately. Asterisk indicates missing data (see Example 1 for explanation).

For the remaining vocal function measures, there were no pretreatment voice assessment data for patients M1 and M2, because both were aphonic and one presented with a tracheotomy, and there were no posttreatment aerodynamic measures for M7 because of technical difficulties. FIG. 4 displays the results for average F0 during the reading of a standard passage with female and male data assessed separately because of normal gender-based differences in vocal pitch (ie, the average female pitch being approximately one octave above the average male pitch). Patient F1 displayed an abnormally elevated F0 before treatment (249 Hz) that then fell to a lower-than-normal value after treatment (161 Hz). The F0 for patient F2 was within the normal range (204 Hz) before treatment, but it decreased to a lowerthan-normal level after treatment (156 Hz). Patient F3 displayed an elevated F0 (259 Hz) before treatment, but a normal F0 (199 Hz) after treatment. Six of the seven male patients had posttreatment F0 values that fell within or closely approximated the normal range. All five of the male patients who had F0 assessments before and after treatment showed improvements in posttreatment F0 values in the form of decreases that ranged from −3 Hz to −122 Hz. Only patient M2 showed a significantly elevated posttreatment F0 value.

Figure 5:
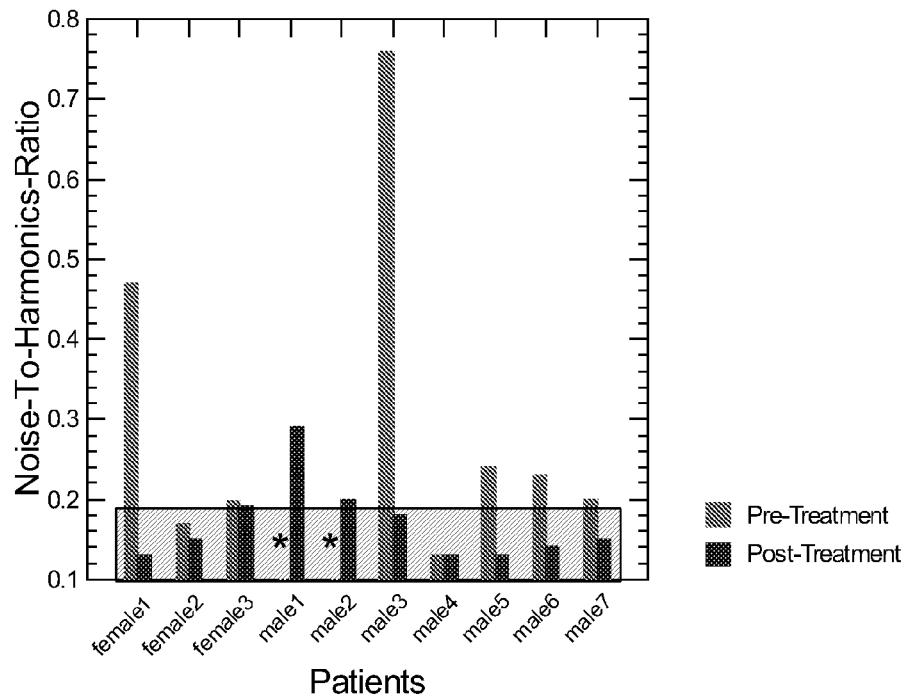
FIG. 5 is a bar graph showing the results from acoustic assessment of noise-to-harmonics ratio during production of sustained vowels before and after treatment. Cross-hatched area indicates range of normal values. Asterisk indicates missing data (see Example 1 for explanation).
Figure 6:
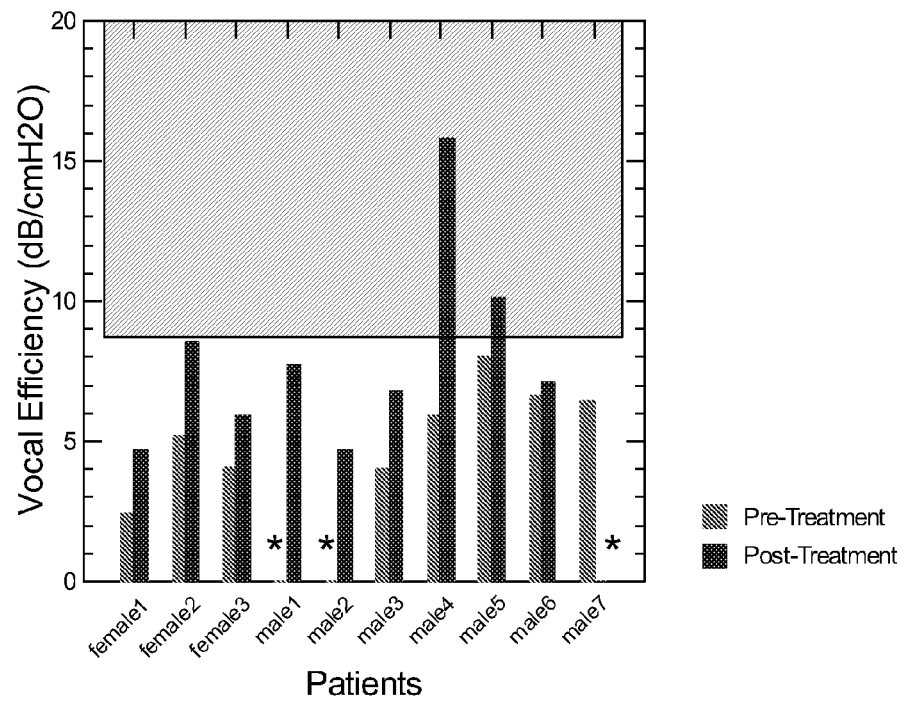
FIG. 6 is a bar graph showing the results from aerodynamic assessment of ratio of sound pressure level to subglottal air pressure (decibels per centimeter of water) during production of standard syllable strings before and after treatment. Cross-hatched area indicates range of normal values. Asterisk indicates missing data (see Example 1 for explanation).

The results for the voice quality-related measure of NHR are shown in FIG. 5. Nine of the ten patients displayed posttreatment NHR values that fell within or closely approximated the normal range. Seven of the eight patients who had NHR assessments before and after treatment showed improvement in posttreatment NHR values that ranged from −0.008 to −0.58, and one patient maintained the same normal NHR value before and after treatment. FIG. 6 shows results for the ratio of sound pressure level to subglottal air pressure (decibels per centimeter of water) during syllable production, which reflects vocal efficiency. Only two of the nine patients who had posttreatment measures attained the normal threshold. However, all seven of the patients who had assessments before and after treatment showed improvements in posttreatment vocal efficiency that ranged from +0.5 to +9.9.

Given the voice problems observed with local injections of cidofovir (vocal fold scarring and intractable hoarseness have been reported (Lee and Rosen, J Voice, 18:551-6 (2004)), the present study proceeded very cautiously in the initial glottal administration of bevacizumab, although there was reasonable comfortable with the limited risk of systemic complications in light of previous uses of the compound. The injection strategy was commensurate with the ophthalmological model, for which there is an extensive literature on the off-label use of bevacizumab with minimal difficulties despite a predominantly elderly population (Fung et al., Br J Ophthalmol 2006; 90:1344-9 (2006); Lynch and Cheng, Ann Pharmacother, 41:614-25 (2007)). Although the doses employed were approximately 5 to 10 times greater than that used for the eye, the present doses were still less than one-fifteenth that of systemic intravenous cancer treatment (Zhu et al., Am J Kidney Dis, 49:186-93 (2007)). The initial two patients who underwent local injections of bevacizumab had ominous chronic airway impairment despite repeated surgery and were compelled by the severity of their disease to try a novel treatment strategy. Initially, only one vocal fold was injected. After observing a dramatic diminishment of the pace of disease recurrence, along with substantial voice improvement, the second vocal fold was treated as well. However, it was difficult to assess the effect of the bevacizumab on the superficial lamina propria (phonatory mucosal pliability), because these patients had substantial prior surgery at other institutions.

Encouraging and dramatic results were noted in all 10 patients; all have had greater than 90% improvement as compared with prior patterns of recurrence with KTP laser treatment alone. Four of the 10 have had resolution so that they no longer have discernible disease. Another four of the 10 have microscopic disease managed solely by office injections of bevacizumab at 8- to 12-week intervals. Only two of the 10 currently require ongoing glottal laser treatment, which is done solely in the office, and the recurrences are very limited as compared with prior recurrence patterns. Both of these patients initially presented with severe disease manifested by airway obstruction, and one of them had a tracheotomy.

The cases reported herein illustrate that patterns of presentation and recurrence in patients with RRP comprise a wide spectrum. Based on the data shown herein, different surgical ablation technologies do not substantially alter recurrence patterns, apart from the fact that easier techniques often led to more complete removal. Effective surgical techniques primarily enable more comprehensive removal of clinically visible disease in a time-efficient fashion while preserving soft tissue and voice. Alternatively stated, the present data do not suggest that any current surgical method that preserves the layered microstructure of the glottis results in a biological change in the papillomatosis- host relationship and/or the recurrence pattern. Accordingly, there will be a spectrum of responses to bevacizumab, with varied patterns of recurrence commensurate with the spectrum of disease presentation.

With regard to voice outcome, the patients displayed substantial improvements in posttreatment vocal function. This was reflected most clearly by the dramatic increases in patients' self-assessments of their voice-related quality of life following the new treatment regimen (see V-RQOL results in FIG. 5). Most patients also had posttreatment improvement in voice quality (see HNR results in FIG. 7) and vocal efficiency, and a majority of patients actually achieved normal posttreatment NHR values. On the other hand, even though vocal efficiency improved in every single case, only two patients achieved completely normal levels (FIG. 8). These results are in line with previous observations that patients with mild persistent phonatory deficits have the capability to adjust underlying aerodynamic parameters to achieve or approximate normal voice quality (Holmberg et al., J Voice, 17:269-82 (2003)).

Stroboscopic observations corroborated the objective vocal function test results. Improvements in voice quality (NHR) and vocal efficiency (decibels per centimeter of water) were reflected by posttreatment improvements in the amplitude and symmetry of vocal fold mucosal wave activity, and by morecomplete glottal closure during phonatory vibratory cycles. The lowered posttreatment F0 values for the female patients were attributed to the vibratory mucosa's being slightly enlarged (mass-loaded) and more pliable, as it appeared to be in the posttreatment stroboscopic examinations of these patients. Stroboscopic observations in the one male patient who displayed a significantly elevated posttreatment F0 value revealed a persistence of adynamic segments of vocal fold mucosa with reduced mucosal wave activity that accompanied the impression of a strained, high-pitched voice, undoubtedly the result of the initial surgical management for his disease.

One goal in introducing bevacizumab as a pharmacologic modulating agent to treat RRP was to diminish the number of office-based laser interventions 12,23 in which the glottal mucosa required ablation. It was previously established that microlaryngoscopic treatment of adult RRP could be mostly avoided, minimizing the morbidity of multiple general anesthetics (Zeitels et al., Aim Otol Rhinol Laryngol, 113:265-76 (2004); Zeitels et al., Aim Otol Rhinol Laryngol, 115:679-85 (2006)). The present results indicate that use of periodic office-based injections of a pharmacologic agent, similar to the model of using Botox for dystonia, is useful for preserving voices and the layered microstructure of vocal folds.

Example 2

Case Study

The patient was a professional singer who developed recurrent respiratory papillomatosis on the vocal folds. Due to its effect on his phonatory membrane, he had to give up his career as a vocalist. He underwent a microlaryngoscopic complete removal of the disease of his phonatory membrane. Over the next two months the disease recurred and worsened. Two months later, he underwent an office-based angiolytic 532 nm KTP laser procedure to eradicate the disease. Three months later he again had substantial recurrence, and two months after that the disease was more prominent than his initial presentation eight months previously.

At that time, the patient had diffuse angiogenic recurrent respiratory papillomatosis involving a substantial amount of the phonatory mucosa bilaterally (vascular spheroid masses on the right vocal fold medially and on the left vocal fold anteriorly) (FIGS. 1A-B). Transoral injection of AVASTIN™ (bevacizumab) was used with infusion of AVASTIN™ into the right and left superficial lamina propria of the phonatory mucosa (FIGS. 1C). A 532 pulsed KTP laser was used to involute the respiratory papillomatosis of the vocal folds, with a 0.3 mm fiber (FIG. 1D; a small amount of white eschar and limited bleeding from the laser treatment of the angiogenic papillomatous lesions was seen on the vocal folds).

Three months later he had limited recurrence and underwent another office-based combined treatment with the angiolytic KTP laser and AVASTIN™ (bevacizumab). On his next visit, three months later, he had no discernable disease and underwent another AVASTINTM injection into the phonatory mucosa bilaterally. He then underwent final bilateral office-based injections of the phonatory vocal folds with AVASTINTM™ one month later though there was no observable recurrence of his disease.

Before bevacizumab injections, this individual developed recurrence in 8 to 10 weeks despite KTP laser treatment. Since completing a series of bevacizumab injections, he has no clinical evidence of disease 6 months after his last injection and has not had a laser procedure in 10 months (FIGS.

1E-F). Most remarkable, his singing is without restriction, comparable to his pre-disease state.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating laryngeal recurrent respiratory papillomatosis (RRP) and maintaining or improving mucosal pliability in the larynx in a human subject, the method comprising locally administering to a phonatory mucosal surface in the larynx of the subject in need thereof an anti-VEGF antibody that binds to human VEGF-A in an amount effective to inhibit RRP and to maintain or improve mucosal pliability in the larynx.

2. The method of claim 1, further comprising a cytoreductive treatment sufficient to debulk a lesion caused by the RRP.

3. The method of claim 1, wherein the anti-VEGF antibody is bevacizumab.

4. The method of claim 1, wherein the local administration to the mucosal surface of the larynx is direct transoral injection into, or topical application onto, a vocal fold, or into or onto mucosal surfaces in the larynx adjacent to the vocal fold.

5. The method of claim 4, wherein the anti-VEGF antibody is administered locally using a controlled-release formulation.

6. The method of claim 2, wherein the cytoreductive treatment is provided by a laser selected from the group consisting of a CO2 laser, an Nd:YAG laser, a Thulium laser; an Er,Cr:YSGG laser; a 532-nm pulsed potassium titanyl phosphate (KTP) laser; or a 585-nm pulsed dye laser (PDL).

7. The method of claim 2, wherein the cytoreductive treatment is provided by cold instruments.

8. The method of claim 2, wherein the cytoreductive treatment is an ablative tissue treatment.

9. The method of claim 1, further comprising administering one or more additional doses of the anti-VEGF antibody at subsequent times.

10. The method of claim 1, wherein the anti-VEGF antibody is ranibizumab.

11. A method of maintaining or improving phonatory mucosal pliability in the larynx in a human subject suffering from a lesion caused by a human papilloma virus (HPV), the method comprising locally administering to a phonatory mucosal surface in the larynx an anti-VEGF antibody that binds to human VEGF in an amount effective to maintain or improve phonatory mucosal pliability in the larynx.

12. The method of claim 11, further comprising a cytoreductive treatment sufficient to debulk the lesion.

13. The method of claim 11, wherein the anti-VEGF antibody is bevacizumab.

14. The method of claim 11, wherein the local administration to the mucosal surface of the larynx is direct transoral injection into, or topical application onto, a vocal fold, or into or onto mucosal surfaces adjacent to the vocal fold.

15. The method of claim 11, wherein the anti-VEGF antibody is administered locally using a controlled-release formulation.

16. The method of claim 12, wherein the cytoreductive treatment is provided by cold instruments.

17. The method of claim 12, wherein the cytoreductive treatment is an ablative tissue treatment.

18. The method of claim 1, further comprising administering one or more additional doses of the anti-VEGF antibody at subsequent times.

19. The method of claim 12, wherein the cytoreductive treatment is provided by a laser selected from the group consisting of a CO2 laser, an Nd:YAG laser, a Thulium laser; an Er,Cr:YSGG laser; a 532-nm pulsed potassium titanyl phosphate (KTP) laser; or a 585-nm pulsed dye laser (PDL).

20. The method of claim 19, wherein the cytoreductive treatment is provided by a 532-nm pulsed potassium titanyl phosphate (KTP) laser.

21. The method of claim 2, wherein the cytoreductive treatment is provided by a 532-nm pulsed potassium titanyl phosphate (KTP) laser.

22. The method of claim 1, wherein the mucosal surface is on at least one of the patient's vocal folds and the anti-VEGF antibody is injected into phonatory mucosa of the vocal fold.

23. The method of claim 22, wherein the anti-VEGF antibody is injected into the superficial lamina propria of the vocal fold.

24. The method of claim 11, wherein the mucosal surface is on at least one of the patient's vocal folds and the anti-VEGF antibody is injected into phonatory mucosa of the vocal fold.

25. The method of claim 24, wherein the anti-VEGF antibody is injected into the superficial lamina propria of the vocal fold.

26. The method of claim 4, wherein the direct transoral injection into the vocal fold comprises injection into the superficial lamina propria.

27. The method of claim 14, wherein the direct transoral injection into the vocal fold comprises injection into the superficial lamina propria.

28. The method of claim 1, wherein the method reduces recurrence of the RRP and improves voice quality of the subject.

29. The method of claim 11, wherein the method reduces recurrence of lesions caused by HPV and improves voice quality of the subject.

\* \* \* \* \*